United States Patent
Selby et al.

(10) Patent No.: US 11,730,198 B2
(45) Date of Patent: Aug. 22, 2023

(54) CLOSED BOTTOM VAPORIZER POD

(71) Applicant: Altria Client Services LLC, Richmond, VA (US)

(72) Inventors: Ryan Selby, Vancouver (CA); Ryan Karkairan, Vancouver (CA)

(73) Assignee: ALTRIA CLIENT SERVICES LLC, Richmond, VA (US)

(*) Notice: Subject to any disclaimer, the term of this patent is extended or adjusted under 35 U.S.C. 154(b) by 0 days.

(21) Appl. No.: 17/527,983

(22) Filed: Nov. 16, 2021

(65) Prior Publication Data
US 2022/0071284 A1    Mar. 10, 2022

Related U.S. Application Data

(62) Division of application No. 16/340,058, filed as application No. PCT/CA2018/050326 on Mar. 16, 2018, now Pat. No. 11,206,869.

(60) Provisional application No. 62/473,154, filed on Mar. 17, 2017.

(51) Int. Cl.
*A24F 40/42*    (2020.01)
*A24F 40/60*    (2020.01)

(52) U.S. Cl.
CPC .............. *A24F 40/42* (2020.01); *A24F 40/60* (2020.01)

(58) Field of Classification Search
None
See application file for complete search history.

(56) References Cited

U.S. PATENT DOCUMENTS

| | | |
|---|---|---|
| 5,093,894 A | 3/1992 | Deevi |
| D720,094 S | 12/2014 | Alima |
| D720,095 S | 12/2014 | Alima |
| 8,915,254 B2 | 12/2014 | Monsees et al. |
| 8,925,555 B2 | 1/2015 | Monsees et al. |
| D747,543 S | 1/2016 | Taha |
| 9,352,288 B2 | 5/2016 | Terry et al. |
| 9,427,711 B2 | 8/2016 | Terry et al. |
| D769,519 S | 10/2016 | Chen |
| D772,478 S | 11/2016 | Liu |
| 9,555,203 B2 | 1/2017 | Terry et al. |
| D780,991 S | 3/2017 | Liu |
| 9,675,109 B2 | 6/2017 | Monsees et al. |

(Continued)

FOREIGN PATENT DOCUMENTS

| | | |
|---|---|---|
| CA | 2748219 A1 | 7/2010 |
| CN | 204217908 U | 3/2015 |

(Continued)

OTHER PUBLICATIONS

Korean Office Action dated Mar. 21, 2023.

(Continued)

*Primary Examiner* — Ross N Gushi
(74) *Attorney, Agent, or Firm* — Harness, Dickey & Pierce, P.L.C.

(57) ABSTRACT

A closed bottom vaporizer pod prevents vaporizable material from exiting the pod and entering into a heat source of a vaporizer. A closed bottom vaporizer pod further reduces contamination and/or fouling of a vaporizer and comprises a closed bottom capsule, at least one air inlet for drawing air into the closed bottom capsule, and at least one air outlet for drawing air out of the closed bottom capsule. An air flow path is created from the at least one air inlet, the closed bottom capsule, and the air outlet which prevents contamination of the vaporizer.

19 Claims, 19 Drawing Sheets

(56) References Cited

U.S. PATENT DOCUMENTS

| | | | |
|---|---|---|---|
| 9,861,772 B2 | 1/2018 | Terry et al. |
| 9,861,773 B2 | 1/2018 | Terry et al. |
| D813,445 S | 3/2018 | Scott |
| D815,342 S | 4/2018 | Sutton |
| D818,639 S | 5/2018 | Kayvon et al. |
| 9,955,732 B2 | 5/2018 | Lin |
| 10,159,278 B2 | 12/2018 | Minskoff et al. |
| 10,561,175 B2 | 2/2020 | Cyphert et al. |
| 10,729,183 B2 | 8/2020 | Janardhan et al. |
| 10,834,964 B2 | 11/2020 | Monsees et al. |
| 2008/0149118 A1 | 6/2008 | Oglesby et al. |
| 2013/0192615 A1 | 8/2013 | Tucker et al. |
| 2015/0351456 A1 | 12/2015 | Johnson et al. |
| 2016/0309784 A1 | 10/2016 | Silvestrini |
| 2016/0324215 A1 | 11/2016 | Mironov et al. |
| 2018/0153220 A1 | 6/2018 | Verleur |
| 2018/0360123 A1 | 12/2018 | Silvestrini |
| 2019/0082732 A1 | 3/2019 | Bautista |
| 2019/0200679 A1 | 7/2019 | Dayioglu et al. |
| 2020/0154757 A1 | 5/2020 | Kahana |
| 2020/0197637 A1 | 6/2020 | Buehler |
| 2020/0205469 A1 | 7/2020 | Fernando et al. |
| 2020/0221759 A1 | 7/2020 | Monsees et al. |
| 2020/0281266 A1 | 9/2020 | Rogan et al. |
| 2020/0305500 A1 | 10/2020 | Liu et al. |
| 2021/0008307 A1 | 1/2021 | Zuber et al. |
| 2021/0052832 A1 | 2/2021 | Spadaro et al. |
| 2021/0068470 A1 | 3/2021 | Campitelli |
| 2021/0120885 A1 | 4/2021 | Xie |
| 2021/0205552 A1 | 7/2021 | Conner et al. |
| 2021/0219616 A1 | 7/2021 | Crump et al. |
| 2021/0227885 A1 | 7/2021 | Sudlow et al. |
| 2021/0235756 A1 | 8/2021 | Qiu et al. |
| 2021/0244082 A9 | 8/2021 | Monsees et al. |
| 2021/0251298 A1 | 8/2021 | Qiu et al. |
| 2021/0337864 A1 | 11/2021 | Conner et al. |
| 2021/0337865 A1 | 11/2021 | Conner et al. |
| 2021/0345667 A1 | 11/2021 | Jackson et al. |
| 2021/0386115 A1 | 12/2021 | Holtz et al. |
| 2022/0000178 A1 | 1/2022 | Crump et al. |
| 2022/0015426 A1 | 1/2022 | Lau et al. |

FOREIGN PATENT DOCUMENTS

| | | |
|---|---|---|
| CN | 105341993 A | 2/2016 |
| CN | 205284992 | 6/2016 |
| CN | 106037011 A | 10/2016 |
| EP | 2978328 A1 | 2/2016 |
| JP | 2009-509523 A | 3/2009 |
| JP | 2015-213516 A | 12/2015 |
| JP | 2019-536070 A | 12/2019 |
| JP | 2020-513768 | 5/2020 |
| KR | 20200145152 A | 12/2020 |
| WO | WO-2007/042941 A2 | 4/2007 |
| WO | 2010073122 A1 | 7/2010 |
| WO | WO-2015/000974 A1 | 1/2015 |
| WO | WO-2015/101479 A1 | 7/2015 |
| WO | 2015128667 A1 | 9/2015 |
| WO | WO-2015/128667 A1 | 9/2015 |
| WO | WO-2015/149403 A1 | 10/2015 |
| WO | WO-2016/00232 A1 | 1/2016 |
| WO | WO-2017/032695 A1 | 3/2017 |
| WO | WO-2017032695 A1 | 3/2017 |
| WO | WO-2018/122389 A1 | 7/2018 |
| WO | WO-2020/039180 A1 | 2/2020 |
| WO | WO-2020/128828 A1 | 6/2020 |
| WO | WO-2020/222496 A1 | 11/2020 |
| WO | WO-2021/151800 A1 | 8/2021 |
| WO | WO-2021/151826 A1 | 8/2021 |
| WO | WO-2021/171182 A1 | 9/2021 |
| WO | WO-2021/228710 A1 | 11/2021 |
| WO | WO-2021/240397 A1 | 12/2021 |
| WO | WO-D209303-001 | 1/2022 |
| WO | WO-D209303-002 | 1/2022 |
| WO | WO-D209303-003 | 1/2022 |

OTHER PUBLICATIONS

Indian Examination Report dated Apr. 11, 2023.
Chinese Office Action dated Nov. 23, 2021.
Chinese Office Action and English translation thereof dated Aug. 5, 2022.
Columbian Office Action dated Jun. 30, 2022.
Columbian Office Action dated May 9, 2022.
Eurasian Office Action dated Mar. 18, 2022.
Israeli Office Action dated May 4, 2022.
Indian Examination Report dated Aug. 6, 2021.
Japanese Office Action and English translation thereof dated May 24, 2022.
Mexican Office Action dated Aug. 20, 2020.
Ukranian Office Action dated Mar. 2, 2021.
International Search Report dated May 18, 2018.
Supplementary European Search Report dated May 12, 2020.
Eurasian Office Action dated Sep. 30, 2020.
European Communication pursuant to Article 94(3) dated Sep. 26, 2022.

CLOSED BOTTOM VAPORIZER POD

FIELD

Embodiments of the present invention generally relate to systems and apparatus containing a vaporizable material, and in particular, relate to closed bottom, vaporizer packets or pods or cartridges containing the vaporizable material therein.

BACKGROUND

Vaporization is a process that involves converting liquids or solids to a gas or vapor without combustion, and typically through heating at a threshold temperature below a combustion temperature of the vaporizable material. When a solid is converted to gas or vapor, the phenomenon is called sublimation. When a liquid is converted to gas or vapor, the phenomenon is called evaporation or boiling. Evaporation is a surface phenomenon, while boiling is a bulk phenomenon. Collectively, sublimation, evaporation, and boiling are referred to as vaporizing, vaporization, and the like, interchangeably, throughout this disclosure.

In the related art, a vaporizer is a device used to vaporize active ingredients of a vaporizable material for the purpose of inhalation by a user. Vaporizable materials may include medicated waxes, e-liquids (such as glycol based vaporizable liquids commonly used in "e-cigarette" or "vaping" apparatus), medicated oils and herbs, including plant materials (typically dried plant materials), such as tobacco, eucalyptus, shisha, blends of plant materials, and other vaporizable materials.

Vaporizers may be portable, such as personal vaporizers which may typically be handheld, and may typically rely on a portable heat source, such as a heating element to heat the vaporizable material until the active ingredients of the vaporizable materials are released, or vaporized, typically by reaching the boiling point of the active ingredients in the vaporizable material. The released vapors of the active ingredients are typically inhaled by the user.

Related art vaporizers may be advantageous to conventional techniques for consuming substances, such as smoking or combustion. It is generally known that smoking substances causes damage to a user's respiratory system and may deliver carcinogens as well as other harmful substances associated with the combustion or partial combustion of a vaporizable material into a user's body. Vaporizers which typically operate at temperatures below the combustion point of the vaporizable material may desirably reduce the amount of carcinogens and other harmful substances emitted and the amount of carcinogens and other harmful substances consumed by the user.

As known in the art, personal vaporizers commonly include a power source, a heat source such as a heating element, an oven or bowl for temporarily containing the vaporizable material and a mouth piece for permitting a user to inhale vaporized materials. In use, a user would fill or pack a vaporizable material into the bowl of the vaporizer and then use the heating element to increase the temperature of the vaporizable material stored or contained within the bowl to above its boiling point, causing the active ingredients therein to vaporize. The vaporized materials, or vapors are then consumed or inhaled by the user through the mouth piece. This is similar to the art of using pipes to smoke tobacco, except that the vaporizable material is not combusted but rather vaporized.

Also similar to the use of pipes to smoke tobacco, after the vaporization of the active ingredients, the bowl of the vaporizer typically must be cleaned out to remove any residue left therein. The process of cleaning the residue is a tedious and time consuming process and insufficient cleaning can lead to degradation of the vaporizer's performance. Further, insufficient cleaning of the bowl can contaminate the bowl, which can impact the enjoyment of a subsequent use.

SUMMARY

In embodiments of the present invention, systems and apparatus for use of a vaporizer pod (also known as packets or cartridges, and used interchangeably herein) can obviate the need to clean a bowl of a vaporizer, and provide a zero-cleaning system by positioning an air inlet to the vaporizer pod external of the vaporizer bowl. Placement of the air inlet, external of the heat source ensures that if any vaporizable materials, residue and/or other contaminants fall out or otherwise exit the vaporizable pod through any openings, such as an air inlet or air outlet, the vaporizable materials, residue and/or other contaminants do not collect within the heat source.

In embodiments of the present invention, a closed bottom vaporizer pod comprises a body having an open top end and an opposing open bottom end. At the bottom end of the body, a capsule containing vaporizable material can be sealingly attached thereto creating a closed bottom vaporizer pod. A mouth piece can be disposed or affixed to the open top end to facilitate a user to draw air from the closed bottom vaporizer pod. In embodiments, the closed bottom vaporizer pod can be placed into a vaporizer and positioned within a heat source of the vaporizer, wherein the vaporizable materials are heated to its boiling temperature by a heat source. The heating of the active ingredients present in the vaporizable materials to its boiling point creates vapors which can be inhaled through the outlet.

In a broad aspect of the invention, a closed bottom vaporizer pod comprises a closed bottom capsule adapted to store vaporizable material therein, at least one air inlet for drawing air into the capsule, and at least one air outlet for drawing air out of the capsule, wherein the at least one air inlet is positioned proximal or adjacent the at least one air outlet and an air flow path is created from the at least one air inlet, the capsule, and the at least one air outlet.

In a broad aspect of the invention, a system for vaporizing vaporizable materials comprises a vaporizer having a heat source, and a capsule adapted to store vaporizable material therein, the capsule comprising at least one air inlet for drawing air into the capsule, and at least one air outlet for drawing air away from within the capsule, wherein the capsule is retained within the vaporizer and the at least one air inlet is positioned external of the heat source.

In another broad aspect of the invention, a vaporizer for accepting a vaporizer pod and permitting an end user to vaporize active ingredients of a vaporizable material stored within the vaporizer pod comprises a housing having an aperture aligned with a chamber for receiving the vaporizer pod therein, a heat source disposed within the housing for providing sufficient heat to the vaporizer pod to vaporize the vaporizable material stored therein, a vacuum insulator disposed within the housing for containing and directing heat in the heat source and towards the closed bottom vaporizer pod, a spacer for spacing away the heat source from the vacuum insulator; and a power source for providing power to the heat source.

DETAILED DESCRIPTION

Figure 1B:
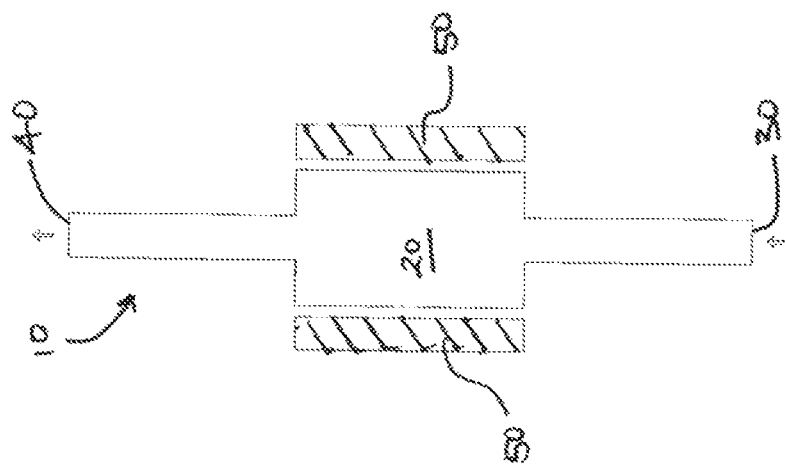
FIG. 1B is a schematic side cross-sectional view of the embodiment in accordance to FIG. 1A, disposed within a heat source.

Applicant notes that there are a variety of ways to reduce the fouling or contamination of a vaporizer bowl by residue left behind after a vaporizable material has been consumed or inhaled by a user.

One common method known in the industry is to clean the heating chamber or bowl after every use. But as previously discussed, insufficient cleaning of the heating chamber can lead to degradation of the heating chamber, and decreased performance of the vaporizer and user experience. Another method known in the prior art for reducing the fouling or contamination is to use replaceable cartridges which contain the vaporizable materials therein. However, using replaceable cartridges does not fully eliminate contamination or the need for cleaning due to open air inlets and outlets to the replaceable cartridges. Furthermore, use of replaceable cartridges can be expensive and is often not environmentally friendly as the cartridges are not recyclable.

Accordingly, embodiments of the present invention provides for a zero-cleaning system and apparatus by eliminating the fouling and/or contamination of the vaporizer bowl.

In an embodiment according to the present invention, a bowl of a vaporizer can be lined with a protective sleeve or liner to isolate the vaporizer bowl from directly coming into contact with a vaporizable material, residues, and/or other contaminants. The liner can be sealed at a bottom end to fully contain the vaporizable material therein, and be opened at the opposite top end for permitting the user to fill or contain the liner with a desired vaporizable material. The vaporizable material can then be vaporized by the heat source in the vaporizer and the resulting vapors can be inhaled by the user. In the vaporizer industry, an open end of the vaporizer pod (also known as a vaporizer packet or cartridge, and used interchangeably herein) is typically placed in the mouth of the user in order to inhale or consume any vaporized materials from the vaporizer pod. This open end is typically referred to as the top end of the vaporizer pod, and accordingly, the distal end therefrom is typically referred to as the bottom end.

The isolation of the exterior surface of the bowl from the vaporizable material obviates the need for the user to clean the bowl of any residue that is created during vaporization of the vaporizable material, increasing the longevity of the bowl and the vaporizer in general, and creates a reliable and consistent performance for increased enjoyment by the end user.

The liner should preferably be made of a material that has a melting point sufficiently greater than a boiling point of the vaporizable material to prevent the liner from melting when vaporizing the vaporizable material contained therein. The liner should also preferably be made of a material that has a boiling point sufficiently greater than the boiling point of the vaporizable material to ensure that the liner does not vaporize and be consumed or inhaled by the user. For example, the liner can be made of a metal or glass.

Nonetheless, while the liner can be used to isolate an exterior surface of the bowl from directly coming in contact with the vaporizable material, the liner itself must still be sufficiently cleaned after every use to ensure that any subsequent use is not contaminated by residue. The process of cleaning the liner remains time consuming and tedious.

Accordingly, in an embodiment, the liner can be made of a material that is relatively easily disposable, obviating the need to clean the liner after each use. In another embodiment, the liner can also be made of a biodegradable material that can be composted, to reduce the overall environmental footprint.

In embodiments, the liner can be a closed bottom capsule which is adapted to be sealingly attached to a body or tubular extension such that it forms a closed bottom vaporizer pod. The tubular extension can be of sufficient length to position the capsule, and the vaporizable materials stored therein, within the heat source of vaporizer and provide sufficient space to permit a user to place their lips about the tubular extension to inhale vaporized material.

In embodiments, closed bottom capsules can be made from any rigid or any flexible material, such as paper, plant cellulose, foil, glass, metal, plastic, or any other suitable material as previously discussed above. In embodiments, the vaporizer pods, capsules or cartridges, can be reuseable, disposable, recyclable, compostable and/or biodegradable. Embodiments of the closed bottom vaporizer pods simplifies loading and unloading of vaporizable materials into and out of vaporizers, reduces the need for cleaning the bowl of vaporizers and provides convenience to users of having pre-filled pods.

In embodiments, the closed bottom vaporizer pod, packets or cartridges, can include a mouth piece for assisting in controlling the flow of air being drawn into the capsule, and the air exiting the capsule when the vaporized active ingredients are inhaled by the user. The increased control of the air flow increases the potency of the vapors and the users does not have to inhale as much surrounding environmental air to inhale the vaporized active ingredients. The mouth piece can be adapted to be in fluid communication with the capsule for increasing the amount of air containing the vapors drawn from within the capsule and concurrently decreasing the amount of air drawn from air surrounding the vaporizer pod, when a user inhales. In an embodiment, the mouth piece can be an integral part of the vaporizer pod, or be a separate component that can be permanently or removably affixed to the vaporizer pod.

A mouth piece fluidly connected to the capsule can be used by the user to directly inhale therethrough, or can be used to draw air into an existing mouth piece or additional component of the vaporizer to temporarily store, analyze, treat, heat, cool, condense, de-condense flavour, transport or otherwise modify before it is inhaled by the user.

A person skilled in the art would understand that in embodiments, the mouth piece can be adjustable in length, and can include a mechanism or component for adjusting the airflow either into and/or out of the mouth piece and/or capsule. In other embodiments, the mouth piece using known methodologies, can be capable of sealing the capsule and/or mouth piece. The mouth piece can also include a screen, filter, valve or other similar device intended to prevent tar, particulate, or other material from entering the mouth piece from the packets and/or exiting the mouth piece into the capsule and/or exiting the mouth piece into the user.

Figure 1A:
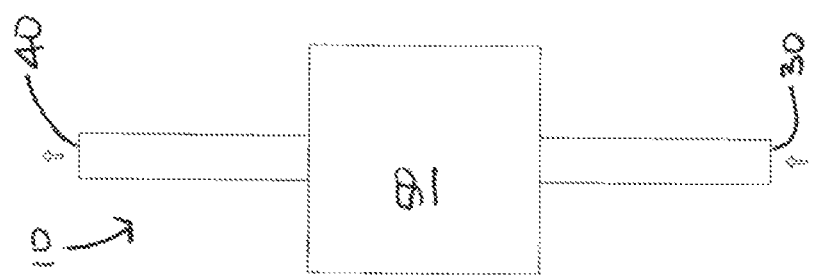
FIG. 1A is a schematic side cross-sectional view of an embodiment of the present invention, illustrating a vaporizer pod comprising a capsule, an air inlet and an air outlet extending away from the capsule, from a bottom of the capsule, and positioned opposite of the air inlet.

With reference to FIGS. 1A and 1B, in an embodiment, a vaporizer pod 10 comprises a capsule 20 for containing vaporizable materials therein, at least one air inlet 30 in fluid communication with the capsule 20 for drawing air into the capsule 20, and at least one air outlet 40 in fluid communication with the capsule 20 for drawing air containing the vapor produced from the vaporized materials therein away from the capsule 20.

As shown in FIG. 1B, the vaporizer pod 10 can be positioned within a heat source 50, such that the capsule 20 is retained within the vaporizer and heat source 50 but the air inlet 30 is positioned outside or external of the heat source 50. Placing the air inlet 30 external of the heat source 50 ensures that any vaporizable materials from the vaporizer pod 10, and particularly the capsule 20, do not exit or fall out of the capsule 20 to enter into and collect within the heat source 50.

Figure 2B:
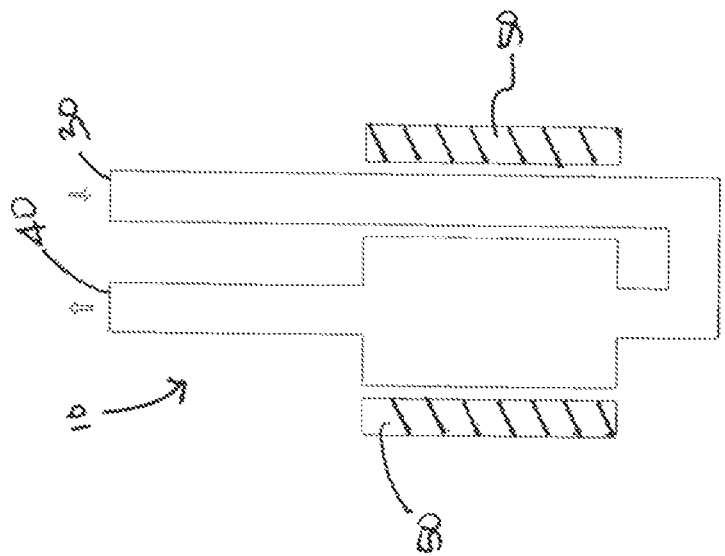
FIG. 2B is a schematic side cross-sectional view of the embodiment in accordance to FIG. 2A, disposed within a heat source.
Figure 2A:
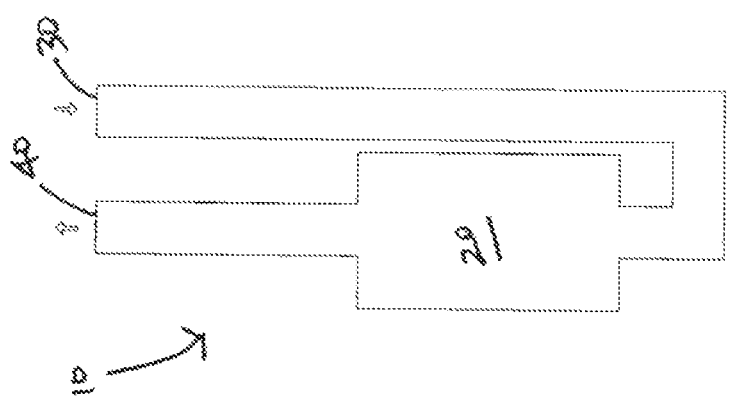
FIG. 2A is a schematic side cross-sectional view of an embodiment of the present invention, illustrating a vaporizable pod comprising a capsule, an air inlet and an air outlet extending away from the capsule, opposite the air inlet, and positioned adjacent the air inlet.

With reference to FIGS. 2A and 2B, and in another embodiment, the at least one air inlet 30 of the vaporizer pod 10 can extend away from the capsule 20 from a bottom of the capsule 20 to be positioned adjacent the at least one air outlet 40, and thereby create a closed bottom capsule.

Figure 3B:
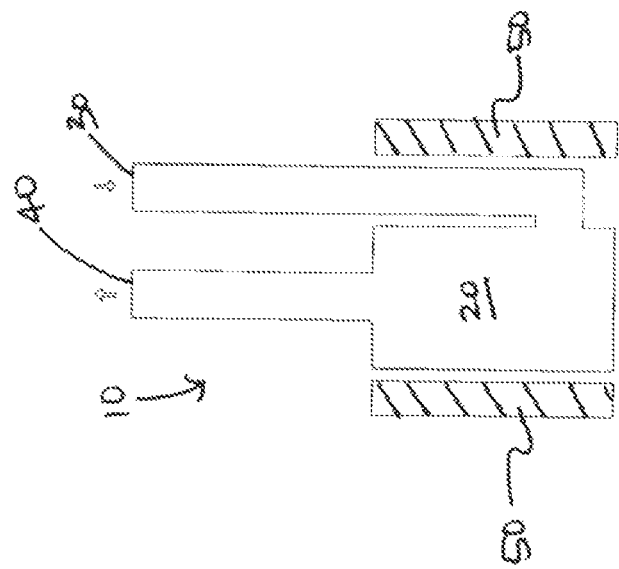
FIG. 3B is a schematic side cross-sectional view of the embodiment in accordance to FIG. 3A, disposed within a heat source.
Figure 3A:
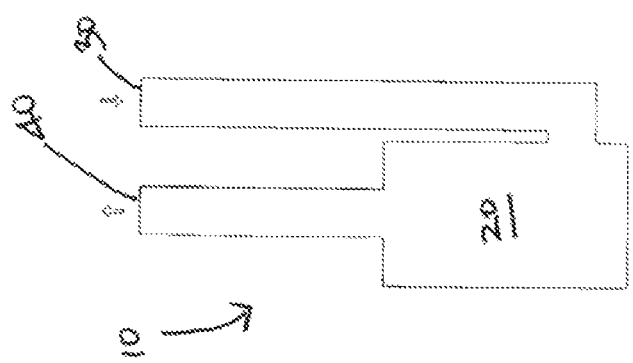
FIG. 3A is a schematic side cross-sectional view of an embodiment of the present invention, illustrating a vaporizable pod comprising a capsule, an air inlet and an air outlet extending away from the capsule, from a side of the capsule, and positioned adjacent the air inlet.

FIGS. 3A and 3B illustrate another embodiment where the at least one air inlet 30 can extend away from the closed bottom capsule 20 from a side thereof, and be positioned adjacent the at least one air outlet 40.

Figure 4B:
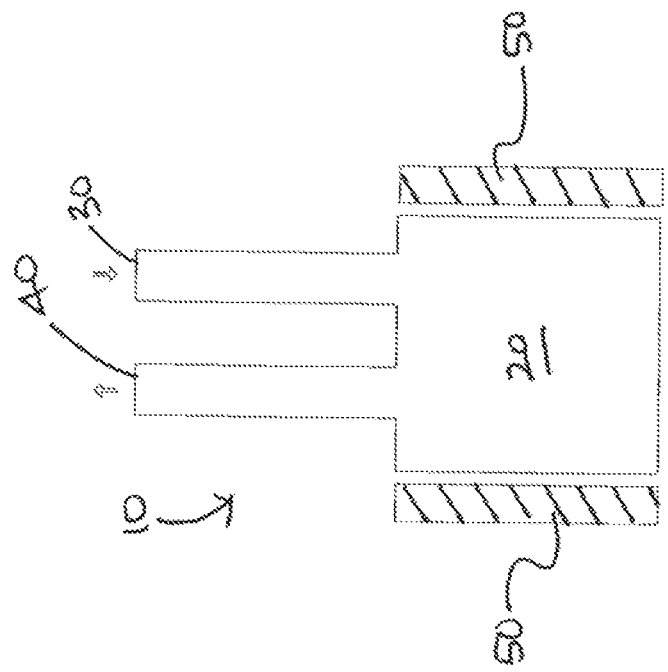
FIG. 4B is a schematic side cross-sectional view of the embodiment in accordance to FIG. 4A, disposed within a heat source.
Figure 4A:
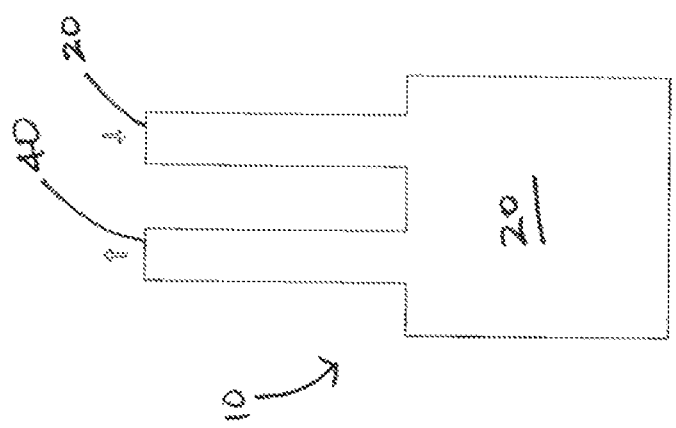
FIG. 4A is a schematic side cross-sectional view of an embodiment of the present invention, illustrating a vaporizable pod comprising a capsule, an air inlet and an air outlet extending away from the capsule, from a top of the capsule, and positioned proximal the air inlet.

FIGS. 4A and 4B illustrate another embodiment where the at least one air inlet 30 can extend away from the closed bottom capsule 20 from a top thereof, and be positioned adjacent the at least one air outlet 40.

Figure 5:
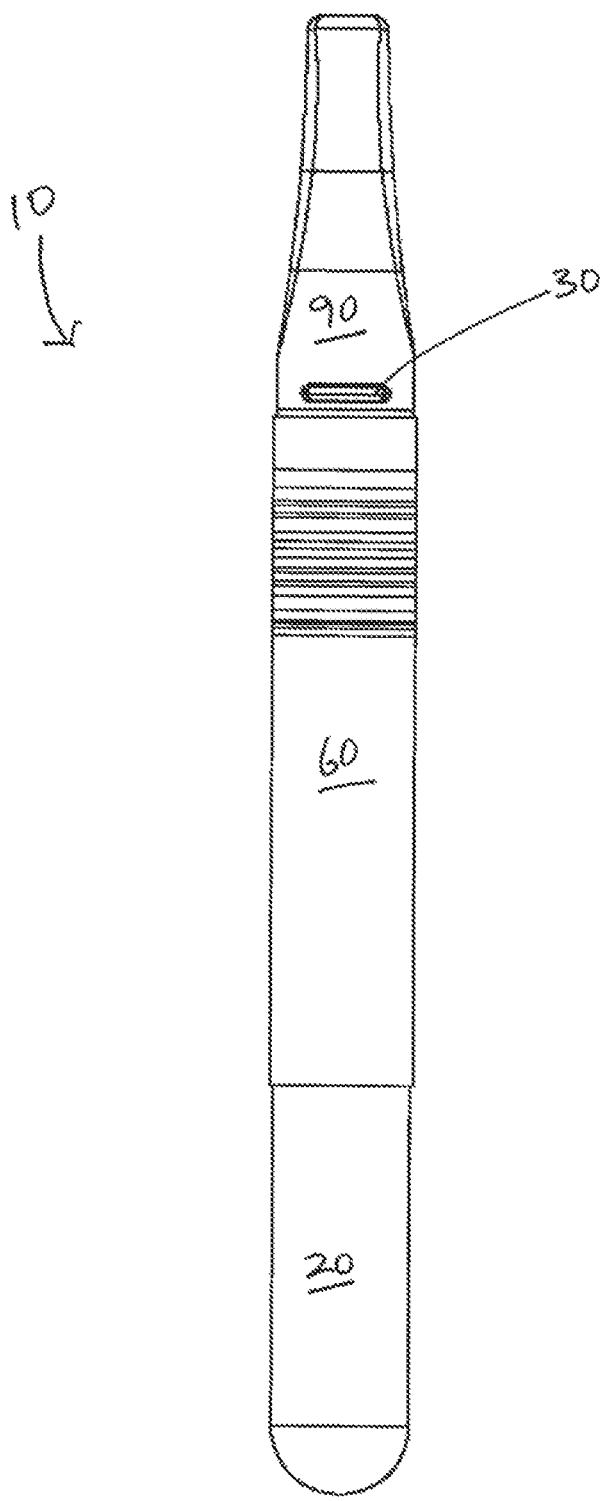
FIG. 5 is a side view of an embodiment of the present invention illustrating a mouth piece, a body having at least one air inlet, and a capsule for storing the vaporizable materials.
Figure 6:
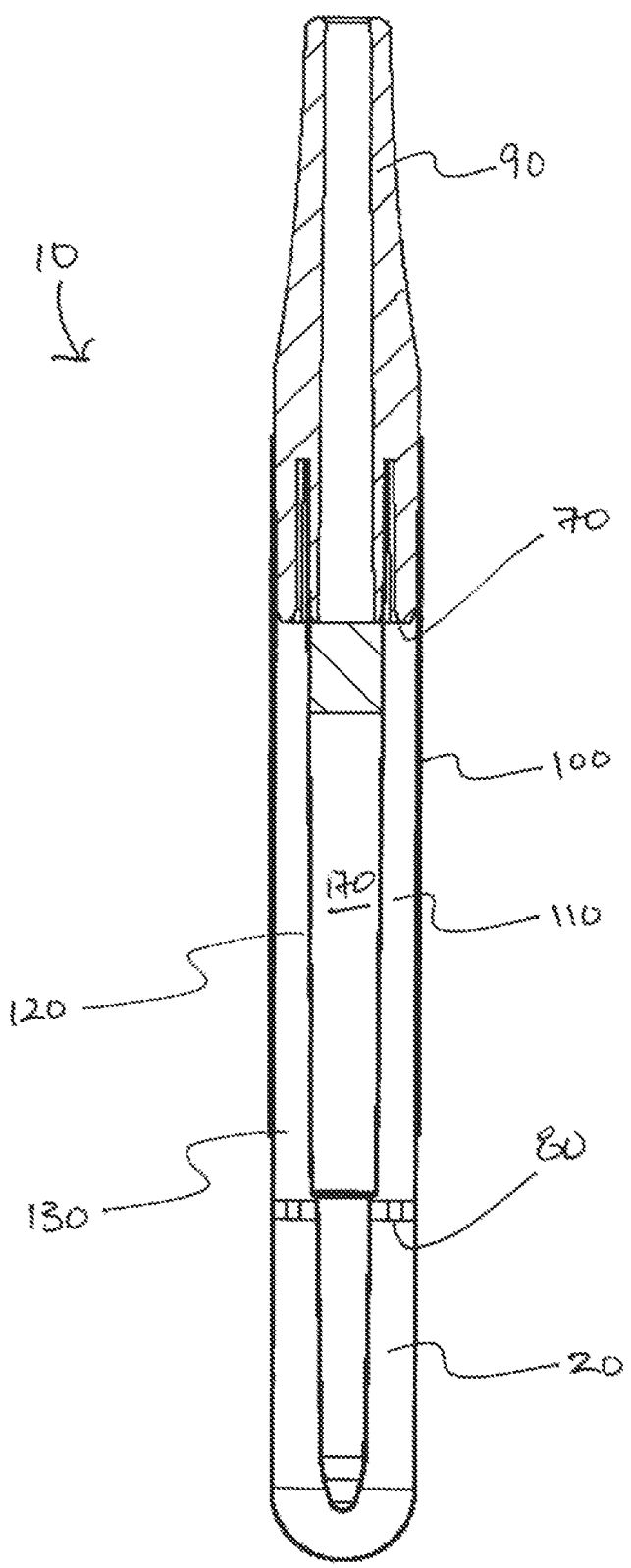
FIG. 6 is a side cross-sectional view of an embodiment of the present invention in accordance to FIG. 5.

With reference to FIGS. 5 and 6, in an embodiment, a closed bottom vaporizer pod 10 comprises a body 60 having an open top end 70 and an open bottom end 80. As shown, a mouth piece 90 can be attached to the open top end 70, and a closed bottom capsule 20 containing vaporizable material is sealingly attached to the bottom end 80.

Shown in greater detail in FIG. 6, the body 60 further comprises an outer tube 100 having an outer annulus 110, and an inner tube 120 disposed within the outer annulus 110, creating an annular space 130 between the outer tube 100 and the inner tube 120. In an embodiment, the inner tube 120 can be concentrically disposed within the outer annulus 110 of the outer tube 100 and have an upper portion 140 extend beyond an upper edge 150 of the outer tube 100. (See FIG. 10). The upper portion 140 defines an upper shoulder 160 of the inner tube 120.

In embodiments, the vaporizer pod 10 can be adapted to incorporate at least one air intake 30 at a top end 70 of the body 60, ensuring that the closed bottom capsule 20 containing the vaporizable material therein is within the interior confines of the capsule 20. Positioning the at least one air intake 30 adjacent to the top end 70 of the body 60 allows a plurality of air intakes to be positioned outside, external of, or spaced away and above a heat source in the vaporizer, ensuring complete isolation of the contents of the closed bottom capsule 20, and preventing contents of the capsule (residue and/or vaporizable material) from directly coming into contact with the exterior surface of the heat source. This complete isolation not only reduces the likelihood of contamination, but obviates the need for cleaning of the vaporizer after use.

With reference back to FIG. 5, at least one air inlet 30 is positioned proximal or adjacent the open top end 70 of the body 60 and is in fluid communication with the annular space 130 created between the outer tube 100 and the inner tube 120. As shown, the annular space 130 extends a length of the body 60 and is in fluid communication with the closed bottom capsule 20.

As shown, the at least one air inlet 30 can be positioned proximal or adjacent a top end 70 of the vaporizer pod 10. In an embodiment, the at least one air inlet can be two or more air inlets from which air to be drawn into the pod 10 and travel therethrough to the closed bottom capsule 20. As shown in FIG. 6, and in embodiments, air can be drawn through the at least one air inlet 30 and travel through at least one inflow passageway to the closed bottom capsule 20. To permit air to be drawn out from the closed bottom capsule 20, the pod 10 can further comprise an outflow passageway, such as the inner annulus 170, isolated from the at least one intake passageway, which extends away from the closed bottom capsule 20. As shown, and in an embodiment, the outflow passageway can be in fluid communication with the mouth piece 90. The outflow passageway can be either permanently or removably attached to the closed bottom capsule 20.

Embodiments incorporating the at least one air inlet 30 above the closed bottom capsule 20 enables the vaporizer pod 10 to be closed at a bottom and be entirely self-contained, where an air flow path begins from outside the heat source and is expelled out of the mouth piece 90, all the while the air flow being fully isolated from any of the exterior surface of the heat source. This allows a completely zero-cleaning system.

Figure 7:
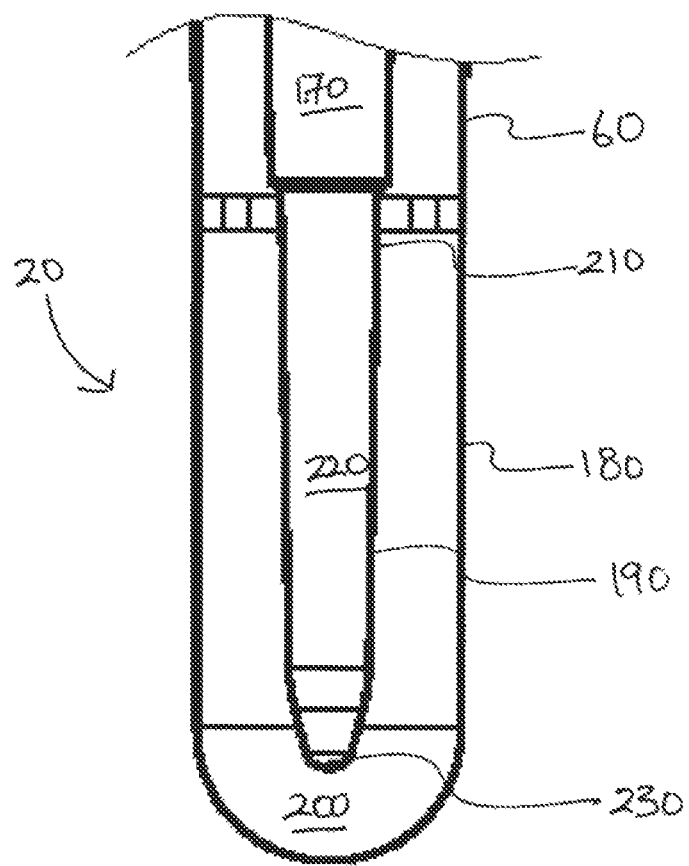
FIG. 7 is a close up side view of the capsule in accordance to FIG. 5.

In an embodiment, and with reference to FIG. 7, the closed bottom capsule 20 can comprise an outer shell 180 fitted over an inner shell 190 for creating a storage cavity 200 for storing vaporizable materials therein. In an embodiment, the inner shell 190 can be concentrically positioned within and connected to the outer shell 180.

As shown, in an embodiment, the inner shell 190 comprises a tubular nipple 210 at a top end thereof and a tubular extension 220 extending axially away from the nipple 210. Adjacent a bottom end of the tubular extension 220 is an aperture 230 for fluidly connecting the storage cavity 200 to the tubular extension 220 and the tubular nipple 210.

Figure 8:
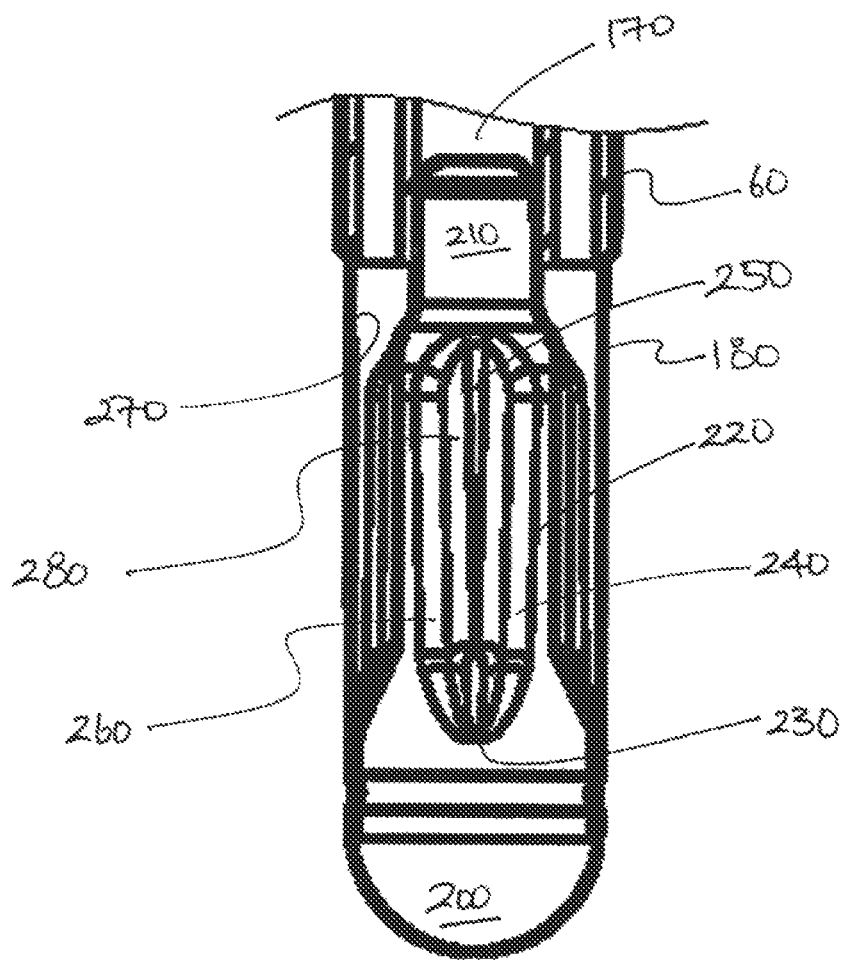
FIG. 8 is a close up side view of an embodiment of the present invention, illustrating a capsule having radially extending fins.

In embodiments, and as shown in FIG. 8, the tubular extension 220 can further comprise at least one radially extending fin 240 for forming at least one groove 250. In the particular embodiment shown in FIG. 8, the at least one radially extending fin 240 further comprises four radially extending fins 240,240,240,240 which define a cross-shaped annular cross-sectional profile. An outside edge 260 of each of the radially extending fins 240 engages an interior surface 270 of the outer shell 180, and in combination with the grooves 250, create at least one air channel 280 which fluidly connect the annular space 130 of the body 60 and the storage cavity 200 of the closed bottom capsule 20.

Referring back to FIG. 6, the combination of the at least one air inlet 30, the annular space 130, the air channels 280, the tubular extension 220 and tubular nipple 210, the inner annulus 170 and the mouth piece 90 all combine to form or create an air flow path, such that when a user places their mouth on the mouth piece 90 and inhales, outside air is drawn from outside the vaporizer and into the annular space 130. The drawn air travels through the annular space 130 and into the storage cavity 200. In an embodiment, the annular space 130 behaves as an inflow passageway. Once the drawn air is within the storage cavity 200, any vaporized materials therein can permeate into and mix with the drawn air.

The drawn air then travels through the aperture 230, through the tubular extension 220 and the nipple 210 and enters into the inner annulus 170. Finally, the drawn air can exit the vaporizer pod 10 through the at least one air outlet 40 and into the mouth piece 90, to be consumed or inhaled by the user. In an embodiment, the inner annulus 170 behaves as an outflow passageway.

Referring back to FIGS. 5 and 6, in an embodiment, the mouth piece 90 can be affixed to and be in fluid communication with the closed bottom capsule 20 via the body 60. Thus, when a user inhales, all of the air drawn out of the closed bottom capsule 20 (or inhaled by the user) will originate from within or inside the interior of the closed bottom capsule 20 and comprise a higher concentration of the vaporized active ingredients.

Figure 9:
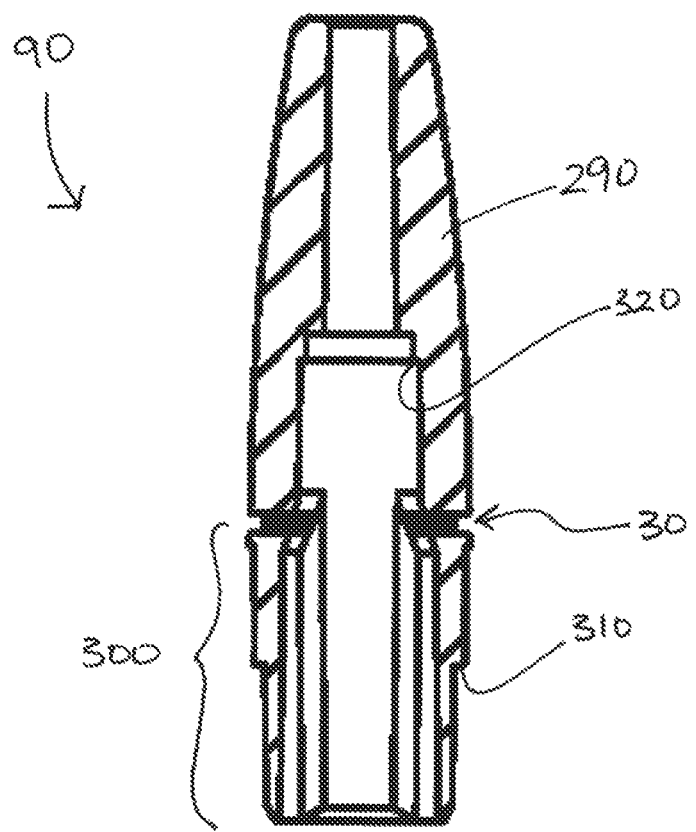
FIG. 9 is a side cross-sectional view of the mouth piece and body in accordance to FIG. 5.

Shown in greater detail in FIG. 9, in an embodiment, the mouth piece 90 can comprise an upper lip portion 290 and a lower tubular wall 300. In embodiments, the lower tubular wall 300 can further comprise a wall shoulder 310 for engaging the upper edge 150 of the outer tube 100.

Figure 10:
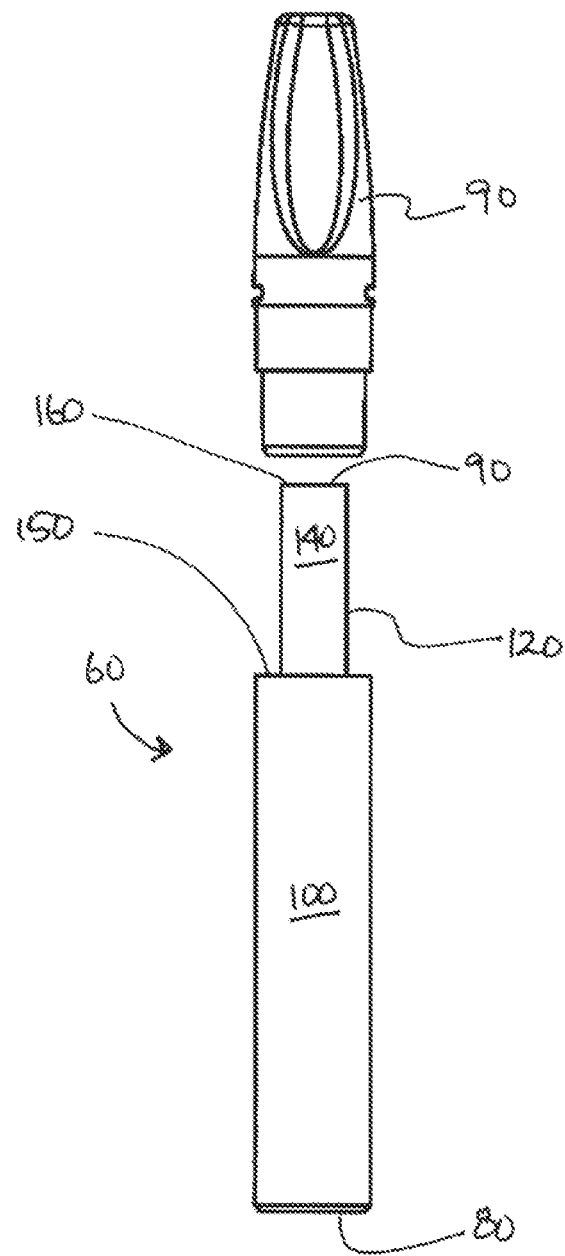
FIG. 10 is a side view of an embodiment of the present invention illustrating a mouth piece and a body having an outer tube and an inner tube.
Figure 11:
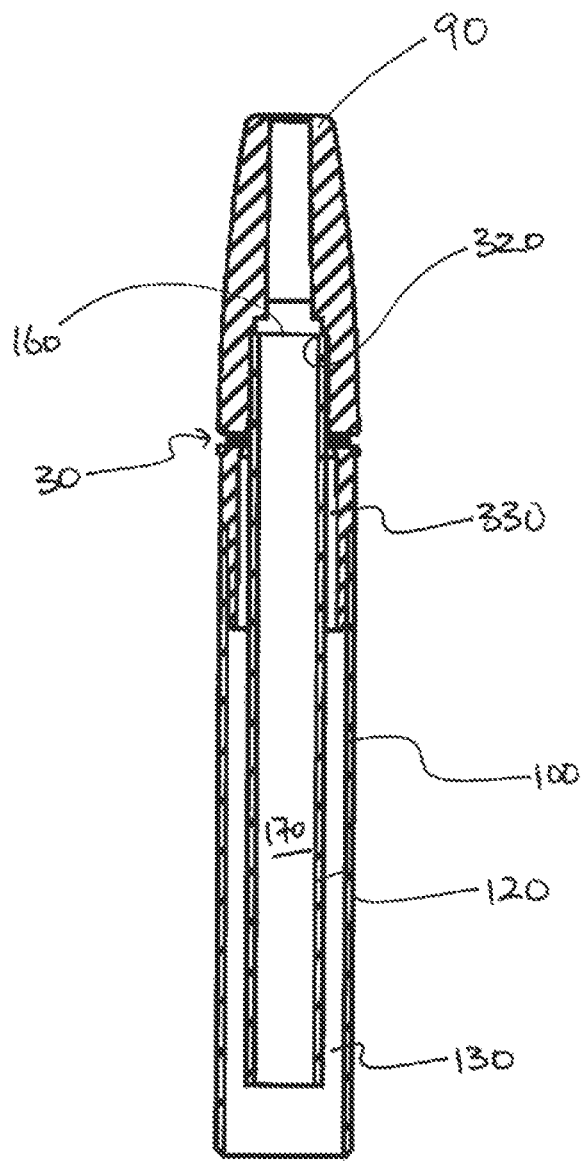
FIG. 11 is a side cross-sectional view of the mouth piece and body in accordance to FIG. 10.

With reference to FIGS. 10 and 11, the mouth piece 90 can be affixed to the body 60. As shown, in an embodiment, the upper portion 140 can extend into the mouth piece 90, and the upper shoulder 160 of the inner tube 120 can engage a lip shoulder 320 of the mouth piece 90. The outer tube 100 can also engage the wall shoulder 310 of the mouth piece 90. The upper portion 140 and the lower tubular wall 300 create a mouth piece air pathway 330 that fluidly connects the annular space 130 and the annular inflow passageway with the at least one air inlet 30.

In embodiments, the mouth piece may be comprised of a single or multiple parts and may be made in any size, shape, form, or design that is suitable. It may be made of a variety of flexible or rigid materials including paper, plant cellulose, foil, glass, metal, plastic, or any other suitable material. It may be disposable, reuseable, recyclable, biodegradable, and/or compostable.

In other embodiments, the air intake and/or outlet may be designed to fit within existing vaporizer mouth pieces or may be designed to replace the mouth piece of a vaporizer or may be designed to work independently or may be designed to work with additional components such as mouth piece extenders, flavored mouth pieces, filters, water-based filtration systems, or other accessories.

Although not shown, in embodiments, the mouth piece can include a mechanism, guide, mount, clip, attachment, or other system for guiding in and/or securing the mouth piece to the vaporizer. In embodiments, the mouth piece can also include a mechanism, guide, mount, clip, attachment, or other system for guiding in and/or securing the packet within the vaporizer. Still in other embodiments, the mouth piece can include a mechanism, guide, mount, clip, attachment, or other system for removing the mouth piece and/or packet from the vaporizer.

Figure 12:
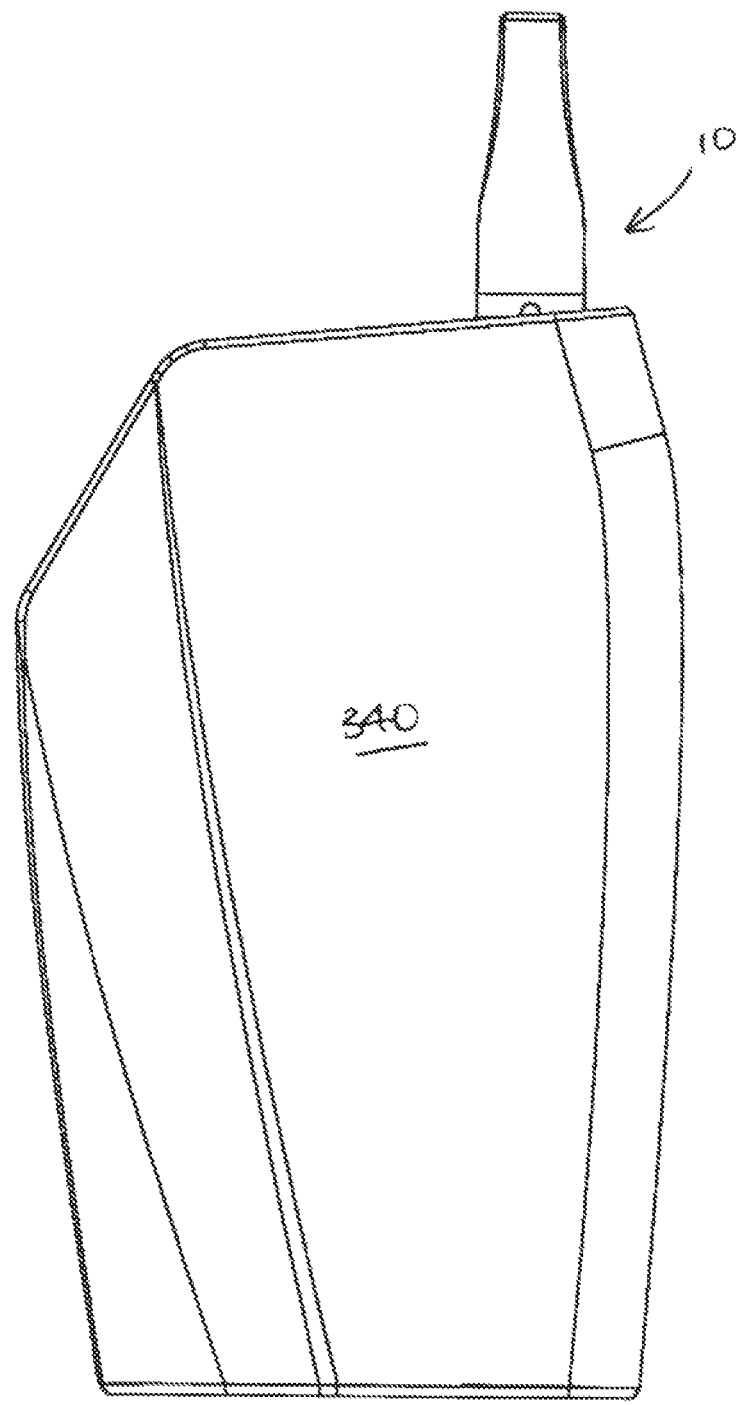
FIG. 12 is a side view of an embodiment of the present invention illustrating a vaporizer adapted to receive a vaporizer pod.

With reference to FIG. 12, in an embodiment, the vaporizer pod 10 can be used in a vaporizer 340 which heats the vaporizable material by conduction. That is, the vaporizer 340 can contain a heat source, and the heat source can be in direct contact with the closed bottom capsule 20 of the pod 10 to heat the closed bottom capsule 20 and the contents therein. As the active ingredients of the vaporizable material is vaporized, the vapors can be inhaled by the user by drawing air into the capsule from the at least one air inlet 30, to mix with the vapors, and then drawn out of the closed bottom capsule 20, and through the mouth piece 90 for consumption by the user. In embodiments using a conductive vaporizer, the air drawn into the pod 10 can be cold.

In an embodiment, the vaporizer pod 10 can be used in the vaporizer 340 which heats the vaporizable material by convection. That is, air is passed through the heat source, and the heated air enters into the closed bottom capsule 20 to heat the vaporizable materials to create vapors. Once the vapors are created, the user can inhale as in the case for conductive vaporizers described above.

In another embodiment, the vaporizer pod 10 can be used in a vaporizer 340 which heats the vaporizable material by radiant heating. That is, infrared heating from a heat source spaced away from the closed bottom capsule 20 can be used to heat the vaporizable material within the closed bottom capsule 20. Similar to embodiments using a conduction as a heating method, the air drawn into the closed bottom capsule 20 can be cold, as the cold air is then heated within the capsule to a temperature sufficient enough to vaporize the active ingredients of the vaporizable material.

In another embodiment, the vaporizer pod 10 can be used in a vaporizer that heats the vaporizable material by conduction, convection, radiant heating, or a combination of any of the three.

Figure 13:
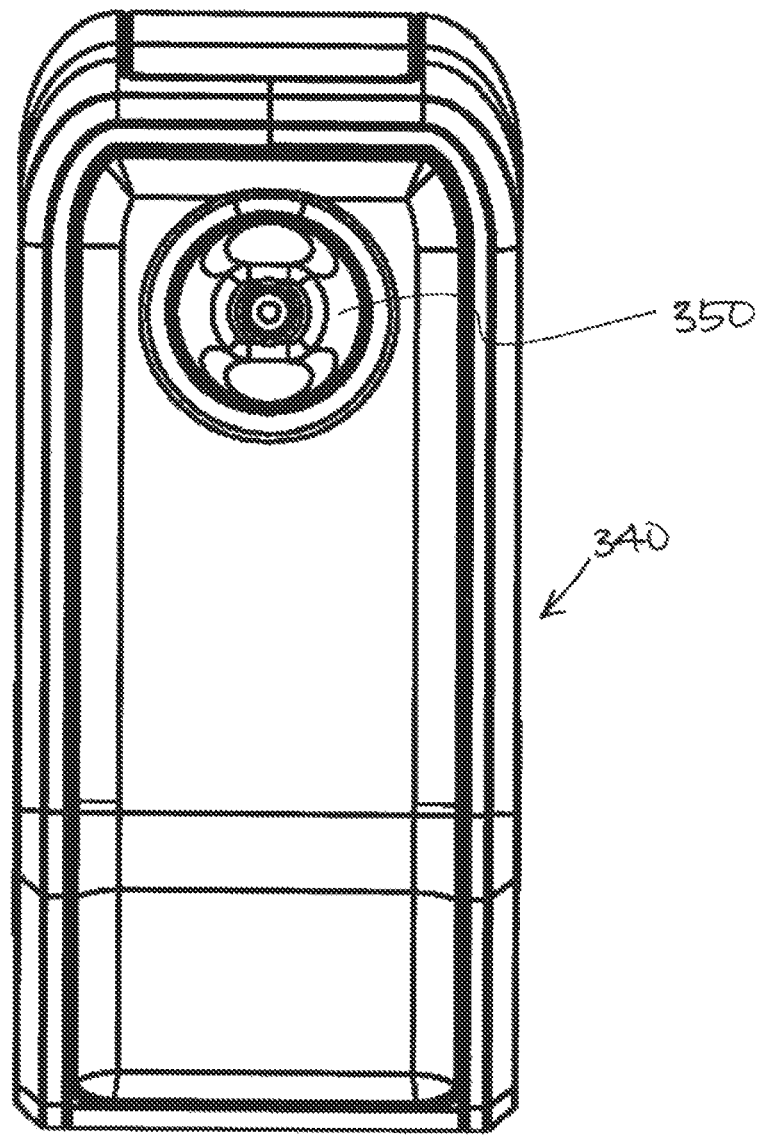
FIG. 13 is a top plan view of the vaporizer in accordance to FIG. 12, illustrating an aperture for receiving a vaporizer pod therethrough.
Figure 14:
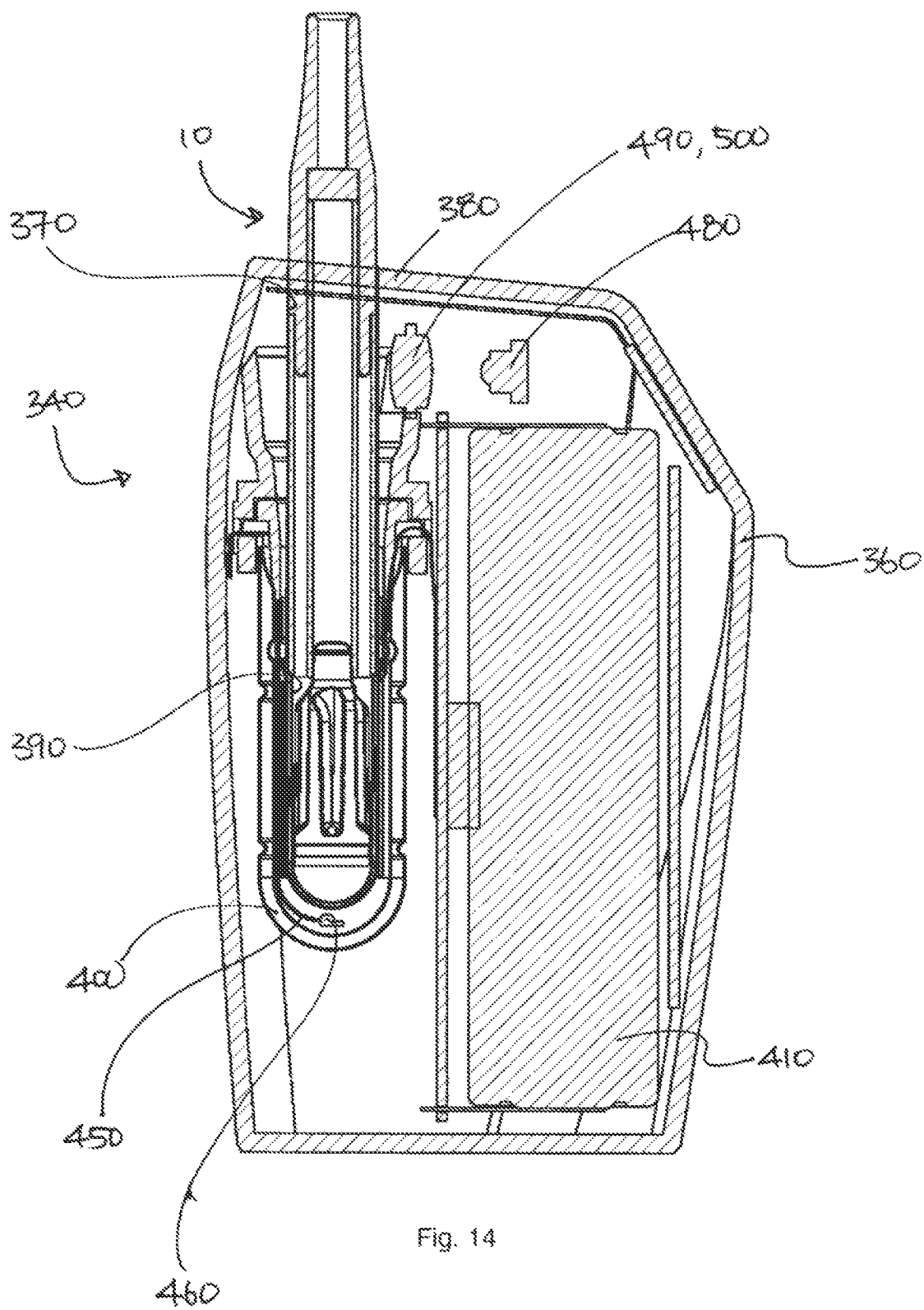
FIG. 14 is a side cross-sectional view of the vaporizer in accordance to FIG. 12, illustrating a heat source, a power source, a three prong cage with a vaporizer pod stop.

With reference to FIG. 13, the vaporizer 340 comprises a vaporizer aperture 350 for receiving a vaporizer pod 10 therethrough. Shown in greater detail in FIG. 14, the vaporizer 340 can comprise a housing 360 defining a chamber 370 which is inline with the vaporizer aperture 350 positioned at a top end 380 of the housing 360, a heat source 390 for providing heat to a vaporizer pod, an insulator 400 and a power source 410. Although not shown in great detail, a person skilled in the art would understand that the heat source 390 receives the closed bottom capsule 20 containing the vaporizable material therein, and the power source 410 is operatively connected to the heat source 390 to provide the necessary power to create heat.

Figure 15:
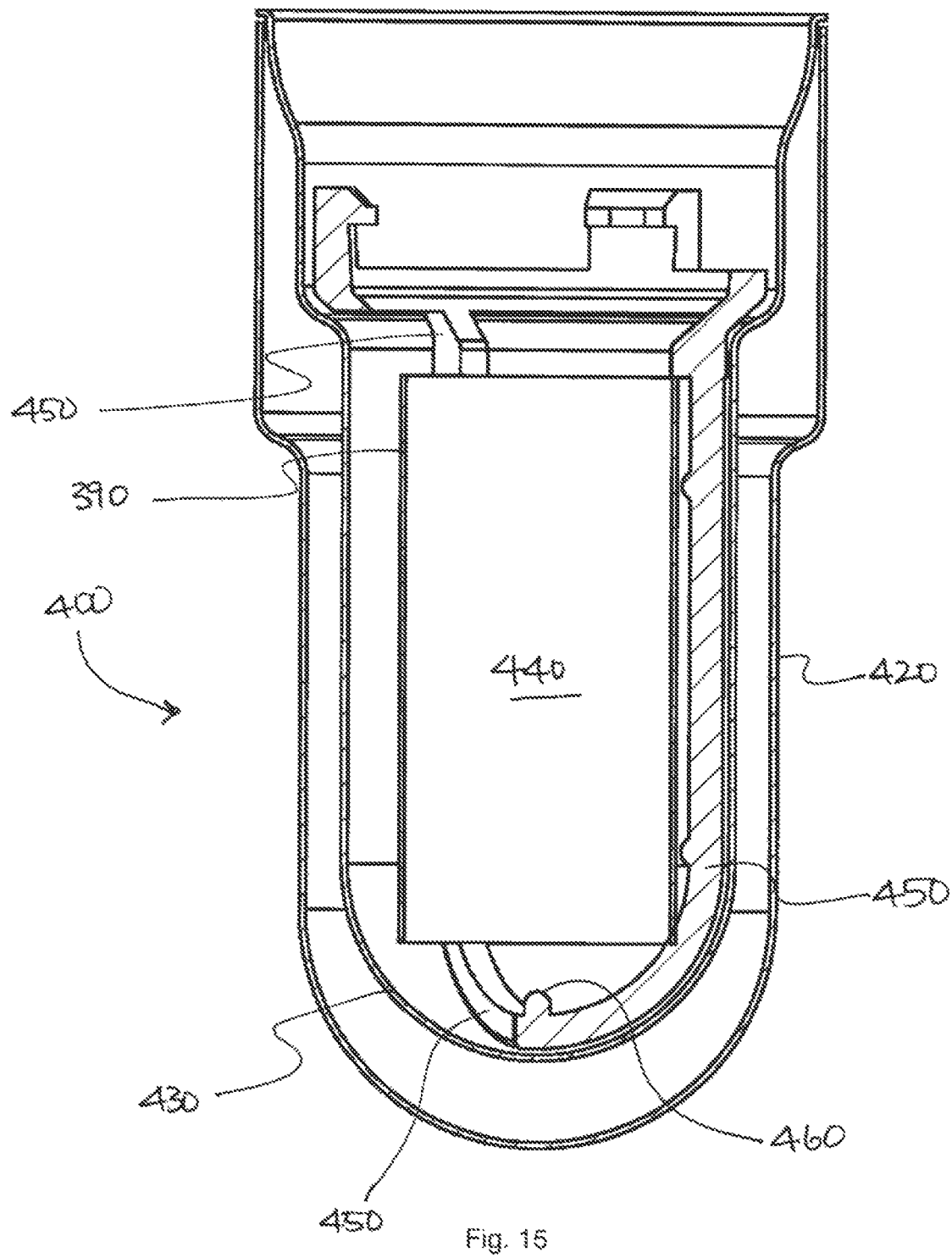
FIG. 15 is a side cross-sectional view of an embodiment of the present invention, illustrating the heat source, cage, and vaporizer pod stop.

With reference to FIG. 15, in an embodiment, the heat source 390 and insulator 400 are shown in isolation from the vaporizer 340. As shown, the insulator 400 can be a vacuum insulated chamber, having an outer wall 420 and an inner wall 430. The insulator 400 maintains heat produced by the heat source 390 within the interior space 440 of the insulating chamber and directs the heat towards the capsule of the vaporizer pod 10. The insulator 400 can increase the efficiency of the vaporizer 340, and thereby reduce heat loss. In embodiments, the insulator 400 can reduce a warm up time of the vaporizer 340 and can increase the life of the power source 410 and the vaporizer 340. In embodiments, the insulator 400 can retain and/or maintain heat in the heat source 390 to increase and maximize efficiency, keep the power source and other components of the vaporizer cool to enable proper functioning and avoid overheating of other components, and keeps the exterior of the vaporizer cool to the touch so that it is comfortable for the user to hold.

As shown, and in embodiments, the insulator 400 can be tubular and have a conical bottom. However, the Applicant notes that the shape of the insulator 400 need not be conical and can be of a shape that would complement the shape of a vaporizer pod being secured therein. In an embodiment, the insulator 400 can simply be a cylindrical tube or other forms of insulators.

As shown, the heat source 390 can be positioned within the interior space 440 of the insulator 400 and be of sufficient size to accept vaporizer pods. Although shown as tubular ring, the heat source 390 can be of various shapes, including coils.

Also as shown, and in embodiments, a spacer 450, such as a cage, prongs, tangs, tubes or other means, can assist in maintaining separation between the heat source 390 and the insulator 400, and can assist in positioning the capsule within the heat source 390.

In an embodiment, and as shown in FIG. 15, the cage 450 can be a three prong cage. In another embodiment, the cage 450 can be a single prong. In another embodiment, the cage 450 can further comprise a vaporizer pod stop 460 for assisting with and/or positioning the closed bottom capsule within the heat source 390.

Figure 16:
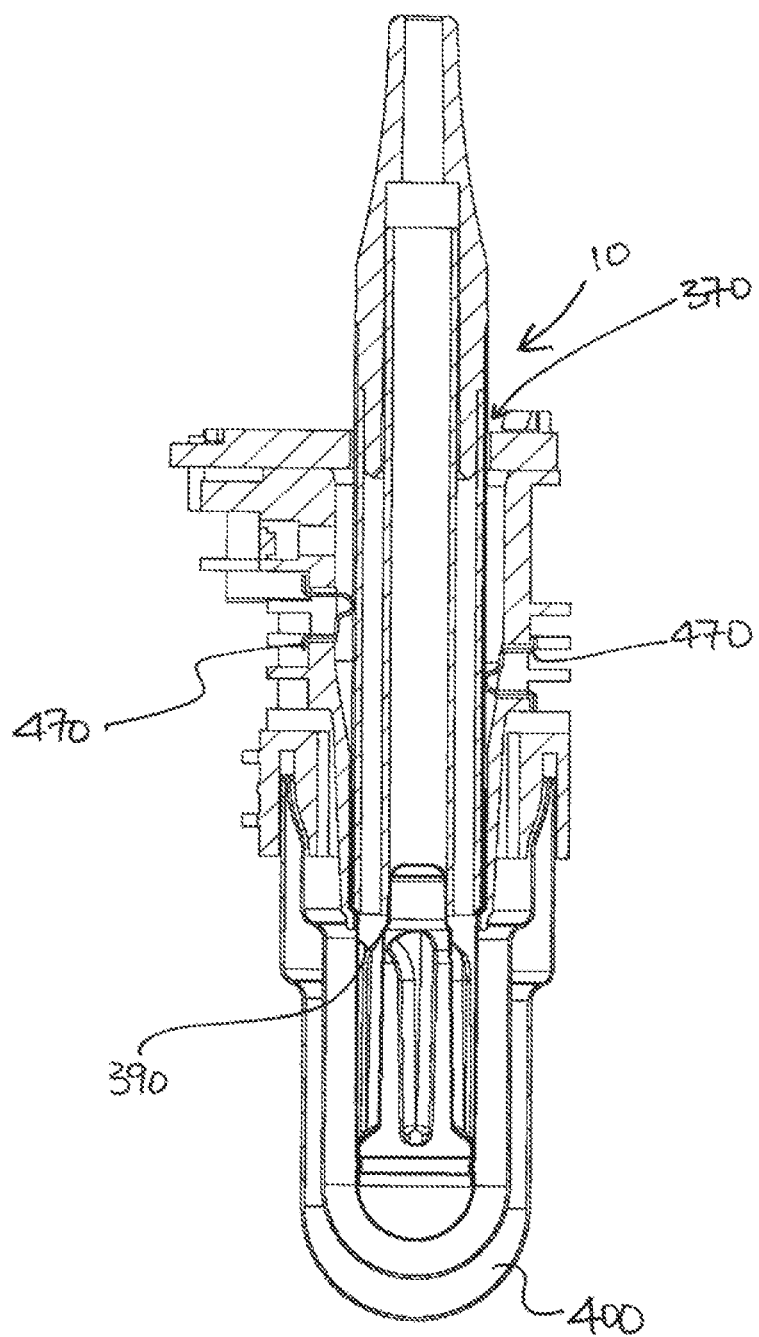
FIG. 16 is a side cross-sectional view of an embodiment of the present invention, illustrating retention means.

With reference to FIG. 16, in embodiments, the vaporizer 340 can comprise retention means 470 for securing a vaporizer pod therein. In embodiments, the retention means 470 can be at least one biasing mechanism which provide force in a direction, such as leaf springs, evenly and circumferentially distributed about the chamber 370 for ensuring that the vaporizer pod 10 is secured within the chamber 370 and the vaporizer 340.

In an embodiment, the retention means 470 can serve a second function to increase safety of use of the vaporizer. When the retention means 470 come into contact with a vaporizer pod 10, the retention means 470 are biased radially outwardly away from the chamber 370. The radially outwardly bias of the retention means 470 can provide a signal to a central processing unit or CPU (not shown) to indicate that a vaporizer pod has been inserted into the vaporizer and that it is safe to provide power to the heat source 390. This secondary function as contact points ensures that power is not unnecessarily provided to the heat source 390 when a vaporizer pod 10 is not present within the vaporizer 340, thereby increasing the lifespan of the vaporizer 340. In embodiments, the retention means 470 can also send a signal to the CPU to indicate that a vaporizer pod is not the vaporizer when the retention means 470 is at its normal resting position, i.e. not biased.

In other embodiments, the signal for indicating whether a vaporizer pod is positioned within the chamber 370 can be accomplished by a secondary means, such as a secondary leaf spring or a safety switch.

In some embodiments, a system for storing machine readable information on each vaporizer pod can be incorporated, along with a system for reading the machine readable information. The machine readable information can include information respecting the vaporizable material contained in each pod, the date that the pod was manufactured, a best before date, the amount of vaporizable material contained therein, the amount of vaporizable material consumed, serial numbers, information regarding the pod or its contents, operation parameters for use with the pod, or other information related or unrelated to the pod. This information can be read-only or read-write information and can be stored on the pod using known technologies, such as printed text, and/or graphics. In embodiments the information can also be stored and machine read using barcodes, RFID, NFC or other visual, electronic, or magnetic communication means.

The machine readable information can also include programming information to automatically control the behavior of the vaporizer by setting an optimal temperature for different vaporizable materials, vaporization times, or provide instructions to increase extra sensory feedback features, such as sounds, haptic feedback, temp changes, etc.

In an embodiment, machine readable information can be written onto the vaporizer pod.

Referring back to FIG. 14, in an embodiment, the machine readable information can be disposed on the vaporizer pod 10 such as a bar code, and can be read using an optical camera 480. In embodiments, the reading of the machine readable information can be enhanced with the assistance of lights 490 and/or lens 500.

The operational parameters, such as optimal temperatures, stored as machine readable information can be relayed to a central processing unit or CPU (not shown) which can control the heat source 390.

Figure 17:
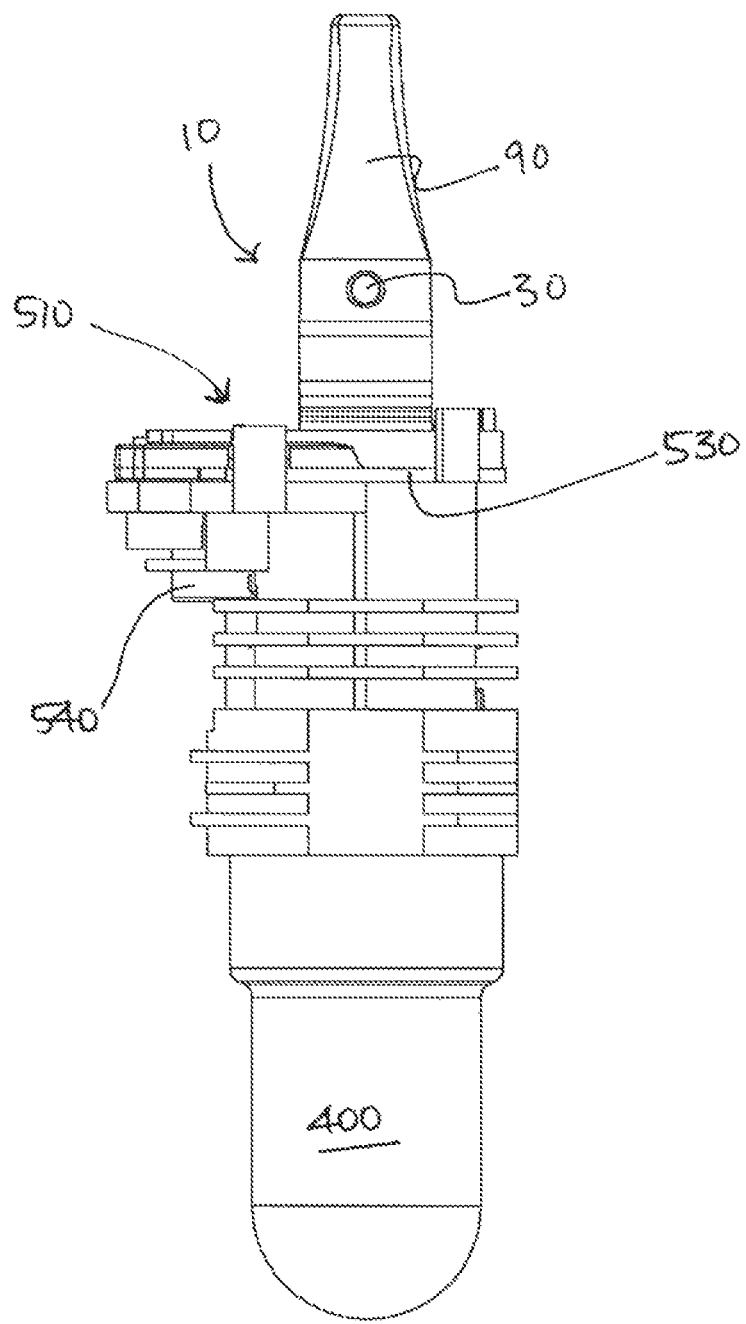
FIG. 17 is a side elevation view of an embodiment of the present invention, illustrating a closure mechanism.
Figure 18A:
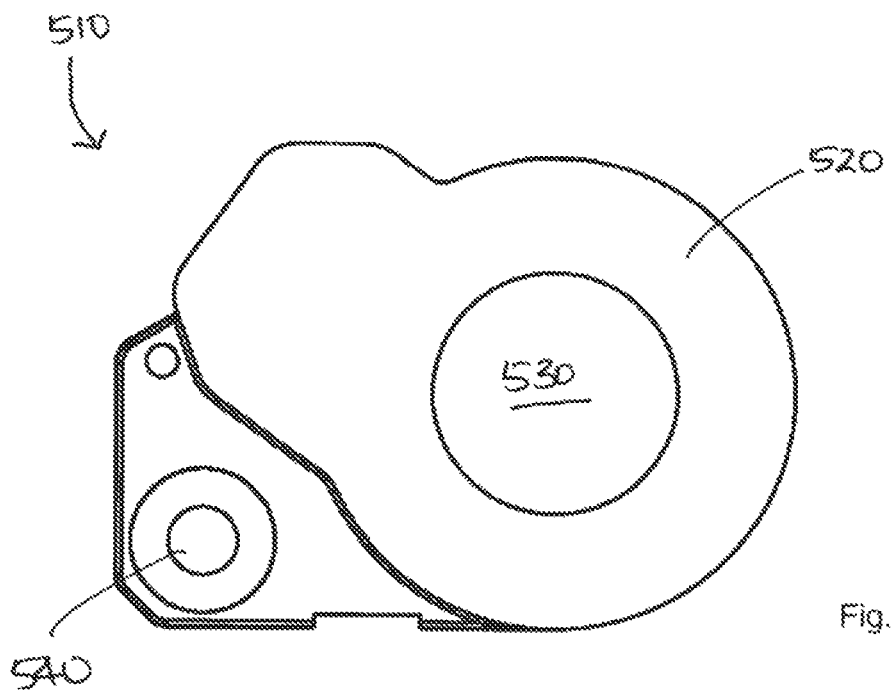
FIG. 18A is a plan view of an embodiment of the present invention illustration an aperture door in its closed position.
Figure 18B:
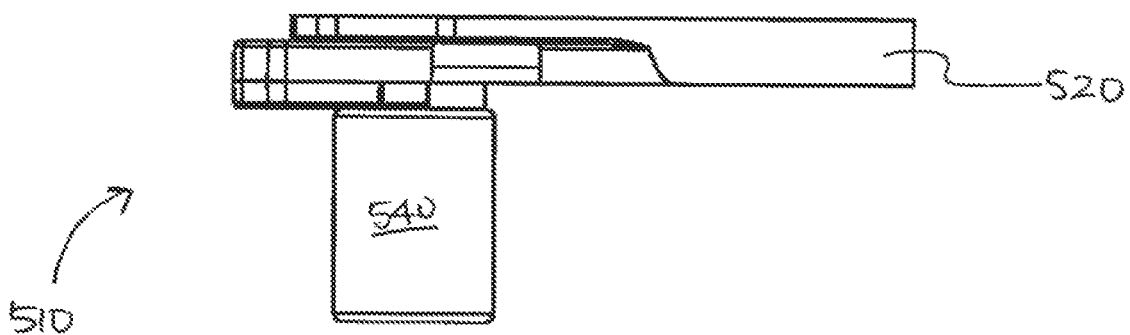
FIG. 18B is a side view of the aperture door in accordance to FIG. 18A.
Figure 19:
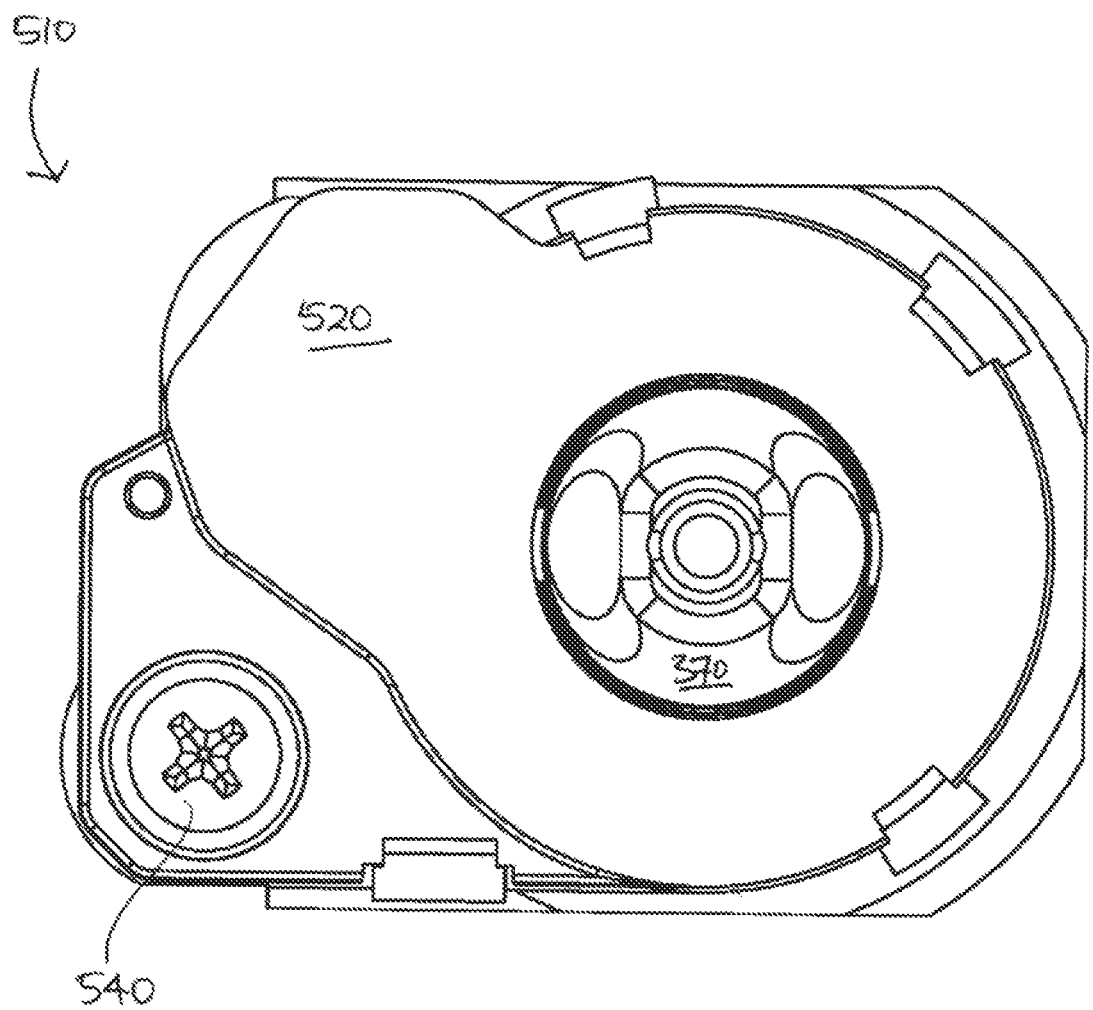
FIG. 19 is a top plan view of the aperture door in accordance to FIG. 18A, in its opened position.

With reference to FIGS. 17 to 19, embodiments of the vaporizer of this present invention can further comprise a closure mechanism 510 which may be closed when the vaporizer is not being used or does not have a vaporizer pod inserted therein. The closure mechanism 510 can mainly comprise a door housing 520 containing a door 530 and a motor 540 for assisting with the opening and/or closure of the door 530. The closing of the door 530 ensures that outside dirt or foreign objects do not accidentally enter into the chamber 370 and cause damage to the interior of the vaporizer 340 and the heat source 390 and insulator 400.

Although not shown, portions of the machine readable information can be displayed to the user on a screen, such as an LED screen, disposed on the housing 340. In an embodiment, Bluetooth® or Wifi or similar technology can be used to transmit or otherwise communicate the machine readable information to a secondary device for display. In embodiments, the machine readable information can also be communicated to the end user audibly, haptically, or visually.

In another embodiment, and using known technology, the power source 410 can be rechargeable. In a particular embodiment, the power source 410 can be recharged using universal serial bus (USB) ports. Yet still, in another embodiment, the vaporizer can have a haptic feedback vibrator.

Information as herein shown and described in detail is fully capable of attaining objects of the present disclosure, and the presently preferred embodiment of the present disclosure, and is, thus, representative of the subject matter which is broadly contemplated by the present disclosure. The scope of the present disclosure fully encompasses other embodiments which may become obvious to those skilled in the art, and is to be limited accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present disclosure.

Moreover, no requirement exists for a system or method to address each and every problem sought to be resolved by the present disclosure, for such to be encompassed by the claims. Furthermore, no element, component, or method step in the present disclosure is intended to be dedicated to the public regardless of whether the element, component, or method step is explicitly recited in the claims. However, that various changes and modifications in form, material, workpiece, and fabrication material detail may be made, without departing from the scope of the present disclosure, as set forth in the claims, as may be apparent to those of ordinary skill in the art, are also encompassed by the present disclosure.

The exemplary embodiments herein described are not intended to be exhaustive or to limit the scope of the disclosure to the precise forms disclosed. They are chosen and described to explain the principles of the disclosure and its application and practical use to allow others skilled in the art to comprehend its teachings.

As will be apparent to those skilled in the art in light of the foregoing disclosure, many alterations and modifications are possible in the practice of this disclosure without departing from the scope thereof.

The invention claimed is:

1. A vaporizer for accepting a vaporizer pod and permitting an end user to vaporize vaporizable material stored within the vaporizer pod, the vaporizer comprising:
   a housing having an aperture aligned with a chamber for receiving the vaporizer pod therein;
   a heat source disposed within the housing for providing sufficient heat to the vaporizer pod to vaporize the vaporizable material stored therein;
   an insulator disposed within the housing for containing and directing heat towards the vaporizer pod;
   a spacer positioned within the insulator for spacing away the heat source from the insulator; and
   a power source for providing power to the heat source.

2. The vaporizer of claim 1, wherein the spacer further comprises a cage.

3. The vaporizer of claim 1, further comprising a retainer configured to retain the vaporizer pod within the vaporizer.

4. The vaporizer of claim 3, wherein the retainer further comprises at least one biasing mechanism circumferentially distributed about the chamber.

5. The vaporizer of claim 1, further comprising a door.

6. The vaporizer of claim 1, wherein the vaporizer pod further comprises:
   machine readable information, the vaporizer further comprises a reader/writer for reading or writing the machine readable information.

7. The vaporizer of claim 6, wherein the machine readable information is communicated to the end user visually, audibly, or haptically.

8. The vaporizer of claim 1, wherein the power source is rechargeable.

9. A system for vaporizing vaporizable materials comprising a vaporizer which comprises:
   a housing having an aperture aligned with a chamber for receiving a capsule therein;
   a heat source disposed within the housing for providing sufficient heat to the capsule to vaporize the vaporizable material stored therein;
   an insulator disposed within the housing for containing and directing heat towards a pod;
   a spacer for spacing away the heat source from the insulator; and a power source for providing power to the heat source.

10. The system of claim 9, wherein the spacer further comprises a cage.

11. The system of claim 9, wherein the vaporizer further comprises a retainer configured to retain the capsule within the vaporizer.

12. The system of claim 11, wherein the retainer further comprises at least one biasing mechanism circumferentially distributed about the chamber.

13. The system of claim 9, wherein the vaporizer further comprising a door.

14. The system of claim 9, wherein the capsule further comprises machine readable information, and wherein the vaporizer further comprises a reader/writer for reading or writing the machine readable information.

15. The system of claim 14, wherein the machine readable information is communicated to an end user visually, audibly, or haptically.

16. The system of claim 9, wherein the power source is rechargeable.

17. An airflow system configured to provide an airflow path in a vaporizing system for vaporizing vaporizable materials, wherein vaporizable material is stored within the airflow path, wherein an airflow path inlet is located proximal to an airflow path outlet, wherein the vaporizing system includes a vaporizer comprising:
- a housing having an aperture aligned with a chamber for receiving the airflow system therein;
- a heat source disposed within the housing for providing sufficient heat to the airflow path to vaporize the vaporizable material stored therein;
- an insulator disposed within the housing for containing and directing heat towards the airflow path;
- a spacer for spacing away the heat source from the insulator; and
- a power source for providing power to the heat source, wherein the airflow system further comprises machine readable information, and wherein the vaporizer further comprises a reader/writer for reading or writing the machine readable information.

18. The airflow system of claim 17, wherein the spacer further comprises a cage.

19. The airflow system of claim 17, wherein the vaporizer further comprises a door.

* * * * *